US011806326B2

(12) United States Patent
Sackner-Bernstein

(10) Patent No.: US 11,806,326 B2
(45) Date of Patent: Nov. 7, 2023

(54) METHODS FOR DOPAMINE MODULATION IN HUMAN NEUROLOGIC DISEASES

(71) Applicant: Jonathan Sackner-Bernstein, Pleasantville, NY (US)

(72) Inventor: Jonathan Sackner-Bernstein, Pleasantville, NY (US)

( * ) Notice: Subject to any disclaimer, the term of this patent is extended or adjusted under 35 U.S.C. 154(b) by 321 days.

(21) Appl. No.: 16/965,466

(22) PCT Filed: Jan. 25, 2019

(86) PCT No.: PCT/US2019/015143
§ 371 (c)(1),
(2) Date: Jul. 28, 2020

(87) PCT Pub. No.: WO2019/147934
PCT Pub. Date: Aug. 1, 2019

(65) Prior Publication Data

US 2021/0052531 A1 Feb. 25, 2021

Related U.S. Application Data

(60) Provisional application No. 62/650,813, filed on Mar. 30, 2018, provisional application No. 62/623,348, filed on Jan. 29, 2018.

(51) Int. Cl.
*A61K 31/198* (2006.01)
*A61K 45/06* (2006.01)
*A61K 47/02* (2006.01)

(52) U.S. Cl.
CPC ............ *A61K 31/198* (2013.01); *A61K 45/06* (2013.01); *A61K 47/02* (2013.01)

(58) Field of Classification Search
None
See application file for complete search history.

(56) References Cited

U.S. PATENT DOCUMENTS

| | | | | |
|---|---|---|---|---|
| 2,868,818 | A | 1/1959 | Pfister et al. | |
| 3,891,768 | A * | 6/1975 | Carlsson | A61K 31/21 514/614 |
| 4,117,161 | A | 9/1978 | Pozuelo | |
| 9,296,739 | B2 | 3/2016 | Sommer et al. | |
| 2011/0207752 | A1 | 8/2011 | Geeganage | |
| 2012/0252791 | A1 | 10/2012 | Blagg | |
| 2014/0073562 | A1* | 3/2014 | Djupesland | A61K 31/4174 514/4.8 |
| 2015/0111937 | A1 | 4/2015 | Hoffman | |
| 2016/0022573 | A1 | 1/2016 | Yacoby-Zeevi | |
| 2017/0056371 | A1 | 3/2017 | Hoffman | |

FOREIGN PATENT DOCUMENTS

| | | | | |
|---|---|---|---|---|
| EP | 0 003 353 | A1 | 8/1979 | |
| EP | 0 373 904 | A1 | 6/1990 | |
| GB | 1 294 812 | A1 | 11/1972 | |
| WO | WO 2009/055925 | A1 | 5/2009 | |
| WO | WO 2010/044981 | A2 | 4/2010 | |
| WO | WO 2013/091008 | A1 | 6/2013 | |
| WO | WO 2014/059052 | A1 | 4/2014 | |
| WO | WO-2015061328 | A2 * | 4/2015 | A61K 31/19 |
| WO | WO 2016/210180 | A2 | 12/2016 | |

OTHER PUBLICATIONS

Brockmann et al. Movement Disorders, vol. 30, No. 3, 2015. (Year: 2015).*
Brusa et al. Functional Neurology 2013; 28(2): 101-105. (Year: 2013).*
Verhoeff et al. Molecular Psychiatry (2002) 7, 322-328. (Year: 2002).*
Engelman et al. "Biochemical and pharmacologic effects of α-methyltyrosine in man," J Clin Invest. 1968;47(3):577-594. (Year: 1968).*
Coppen A. et al., "Levodopa and L-Tryptophan Therapy in Parkinsonism", Manufacturing Processes for the Lancet, Mar. 25, 1972, pp. 654-658, vol. 299, No. 7752, Amsterdam, NL, XP008056731, (five (5) pages).
Khakimova G. R. et al., "Reversible Pharmacological Induction of Motor Symptoms in MPTP-Treated Mice at the Presymptomatic Stage of Parkinsonism: Potential Use for Early Diagnosis of Parkinson's Disease", Molecular Neurobiology, May 19, 2016, pp. 3618-3632, vol. 54, No. 5, XP036244678, (15 pages).
Tabrez S. et al., "A Synopsis on the Role of Tyrosine Hydroxylase in Parkinson's Disease", CNS & Neurological Disorders, May 1, 2012, pp. 395-409, vol. 11, No. 4, XP55872202, (30 pages).
Park S. S. et al., "Disruption of dopamine homeostasis underlies selective neurodegeneration mediated by α-synuclein", European Journal of Neuroscience, Nov. 14, 2007, pp. 3104-3112, vol. 26, No. 11, XP55872479, (nine (9) pages).
Sakka N. et al., "Dopamine is involved in selectivity of dopaminergic neuronal death by rotenone", Neuropharmacology and Neurotoxicology, Dec. 19, 2003, pp. 2425-2428, vol. 14, Issue 18, XP55873759, Retrieved from the Internet: URL:https://journals.1ww.com/neuroreport/Abstract/2003/12190/Dopamine_is_involved_in_selectivity_of.27.aspx (Abstract) (three (3) pages).
Espinosa-Oliva A. M. et al., "Role of dopamine in the recruitment of immune cells to the nigro-striatal dopaminergic structures", NeuroToxicology, Jan. 6, 2014, pp. 89-101, XP028831920, (13 pages).
Yoshimoto Y. et al., "L-dopa and dopamine enhance the formation of aggregates under proteasome inhibition in PC12 cells", FEBS Letters, Jan. 21, 2005, pp. 1197-1202, vol. 579, No. 5, XP029243251 (six (6) pages).
Chen C. X.-Q. et al., "Synaptophysin enhances the neuroprotection of VMAT2 in MPP+-induced toxicity in MN9D cells", Neurobiology of Disease, Aug. 1, 2005, pp. 419-426, vol. 19, No. 3, XP004977685, (eight (8) pages).

(Continued)

*Primary Examiner* — Jeffrey S Lundgren
*Assistant Examiner* — Michael J Schmitt
(74) *Attorney, Agent, or Firm* — Crowell & Moring LLP

(57) ABSTRACT

A method of treating Parkinson's Disease, Huntington's Disease and the like, diseases with abnormal dopamine-neuro-transmission, using small molecules administered systemically that penetrate into the central nervous system to inhibit the rate-limiting step of dopamine synthesis in the central nervous system, the conversion of L-tyrosine to L-3, 4-dihydroxyphenylalanine (L-DOPA) by tyrosine hydroxylase along with its cofactors tetrahydrobiopterin and iron ($Fe^+$).

27 Claims, 5 Drawing Sheets

(56) References Cited

OTHER PUBLICATIONS

Extended European Search Report issued in European Application No. 19743789.0 dated Jan. 5, 2022 (15 pages).
Sackner-Bernstein J., "Estimates of Intracellular Dopamine in Parkinson's Disease: A Systematic Review and Meta-Analysis," Journal of Parkinson's Disease, 2021, pp. 1-8 (eight (8) pages).
Venda et al., "α-Synuclein and dopamine at the crossroads of Parkinson's disease", Europe PMC Funders Group, Author Manuscript, Trends Neurosci., Dec. 2010, pp. 1-21, vol. 33, No. 12, Elsevier Ltd., 21 pages.
Umezawa et al., "A New Microbial Product, Oudenone, Inhibiting Tyrosine Hydroxylase", The Journal of Antibiotics, Oct. 1970, pp. 514-518, vol. XXIII, No. 10, five pages.
Udenfriend et al., "Inhibitors of Purified Beef Adrenal Tyrosine Hydroxylase", Biochemical Pharmacology, 1965, pp. 837-845, vol. 14, Pergamon Press Ltd., 10 pages.
Timmins, "Deuterated drugs; where are we now?", HHS Public Access, Author manuscript, Expert Opin Ther Pat., Oct. 2014, pp. 1-19, , vol. 24, No. 10, 19 pages.
"Xenazine (tetrabenazine) Tablets", May 2008, Prestwick Pharmaceuticals, Inc., 63 pages.
Sjoerdsma et al., "Inhibition of Catecholamine Synthesis in Man with Alpha-Methyl-Tyrosine, an Inhibitor of Tyrosine Hydroxylase", The Lancet, Nov. 27, 1965, pp. 1092-1094, three pages.
Perez et al., "A Role for α-Synuclein in the Regulation of Dopamine Biosynthesis", The Journal of Neuroscience, Apr. 15, 2002, pp. 3090-3099, vol. 22, No. 8, ten pages.
"Parkinson's disease in adults: diagnosis and management", NICE guideline NG71, Methods, evidence and recommendations, National Institute for Health and Care Excellence, Jul. 2017, 243 pages.
Ogawa et al., "L-DOPA treatment from the viewpoint of neuroprotection: Possible mechanism of specific and progressive dopaminergic neuronal death in Parkinson's disease", J Neurol, 2005, pp. IV/23-IV/31, vol. 252, nine pages.
Nagatsu et al., "Tyrosine Hydroxylase", The Journal of Biological Chemistry, Sep. 1964, pp. 2910-2917, vol. 239, No. 9, nine pages.
Moon et al., "Mitochondrial Dysfunction in Parkinson's Disease", Experimental Neurobiology, Jun. 2015, pp. 103-116, vol. 24, No. 2, 14 pages.
Meiser et al., "Complexity of dopamine metabolism", Meiser et al. Cell Communication and Signaling, BioMed Central, 2013, pp. 1-18, vol. 11, No. 34, 18 pages.
Lohr et al., "VMAT2 and Parkinson's disease: harnessing the dopamine vesicle", HHS Public Access, Author manuscript, Expert Rev Neurother., Oct. 2014, pp. 1-6, vol. 14, No. 10, six pages.
Levitt et al., "Elucidation of the Rate-Limiting Step in Norepinephrine Biosynthesis in the Perfused Guinea-Pig Heart", The Journal of Pharmacology and Experimental Therapeutics, 1965, pp. 1-8, vol. 148, No. 1, The Williams & Wilkins Co., eight pages.
"Highlights of Prescribing Information" Ingrezza (valbenazine), Apr. 2020, pp. 1-16, 18 pages.
Hirsch et al., "Melanized dopaminergic neurons are differentially susceptible to degeneration in Parkinson's disease", Jul. 28, 1988, pp. 345-348, vol. 334, Nature Publishing Group, four pages.
Haruki et al., "Tetrahydrobiopterin Biosynthesis as an Off-Target of Sulfa Drugs", Science, AAAS, May 24, 2013, pp. 987-991, vol. 340, six pages.
Hartmann, "Postmortem studies in Parkinson's disease", Basic research, Dialogues Clin. Neurosci., 2004, pp. 281-293, 13 pages.
Fahn, "The 200-year journey of Parkinson disease: Reflecting on the past and looking towards the future", Parkinsonism and Related Disorders, 2018, pp. S1-S5, vol. 46, Elsevier, five pages.
Fahn et al., "Levodopa and the Progression of Parkinson's Disease", The New England Journal of Medicine, Dec. 9, 2004, pp. 2498-2508, vol. 351, 11 pages.
Engelman et al., "Metabolism of α-Methyltyrosine in Man: Relationship to Its Potency as an Inhibitor of Catecholamine Biosynthesis", The Journal of Clinical Investigation, 1968, pp. 568-576, vol. 47, nine pages.
Damier et al., "The substantia nigra of the human brain II. Patterns of loss of dopamine-containing neurons in Parkinson's disease", Brain, 1999, pp. 1437-1448, vol. 122, Oxford University Press, 12 pages.
Conway et al., "Kinetic Stabilization of the α-Synuclein Protofibril by a Dopamine-α-Synuclein Adduct", Science, Nov. 9, 2001, pp. 1346-1349, vol. 294, five pages.
Chen et al., "Dopamine imbalance in Huntington's disease: a mechanism for the lack of behavioral flexibility", frontiers in Neuroscience, Jul. 4, 2013, pp. 1-14, vol. 7, No. 114, 14 pages.
Cepeda et al., "The Role of Dopamine in Huntington's Disease", HHS Public Access, Author manuscript, Prog Brain Res., 2014, pp. 1-18, vol. 211, 18 pages.
Bronstein et al., "Deep Brain Stimulation for Parkinson Disease", Neurological Review, Arch Neurol, Feb. 2011, pp. 165-171, vol. 68, No. 2, seven pages.
Brogden, "α-Methyl-p-Tyrosine: A Review of its Pharmacology and Clinical Use"J-Serial Periodical, Mar. 1981, pp. 81-89, vol. 21, No. 2, 10 pages.
Bernheimer et al., "Brain Dopamine and the Syndromes of Parkinson and Huntington, Clinical, Morphological and Neurochemical Correlations", Journal of the neurological Sciences, 1973, pp. 415-455, vol. 20, Elsevier Scientific Publishing Company, Amsterdam, 45 pages.
Ayukawa et al., "Inhibition of Tyrosine Hydroxylase by Aquayamycin", The Journal of Antibiotics, May 1968, pp. 350-353, four pages.
Uttamsingh et al., "Altering Metabolic Profiles of Drugs by Precision Deuteration: Reducing Mechanism-Based Inhibition of CYP2D6 by Paroxetine", The Journal of Pharmacology and Experimental Therapeutics, Jul. 2015, pp. 43-54, vol. 354, No. 1, The American Society for Pharmacology and Experimental Therapeutics, 16 pages.
Udenfriend et al., "Inhibitors of Purified Beef Adrenal Tyrosine Hydroxylase", Biochemical Pharmacology, 1965, pp. 837-845, vol. 14, No. 5, Pergamon Press Ltd., Great Britain, 10 pages.
Pandey et al., "Striatal dopamine level contributes to hydroxyl radical generation and subsequent neurodegeneration in the striatum in 3-nitropropionic acid-induced Huntington's disease in rats", Neurochemistry International, 2009, pp. 431-437, vol. 55, No. 6, Elsevier, seven pages.
Lecht et al., "Rasagiline—a novel MAO B inhibitor in Parkinson's disease therapy", Therapeutics and Clinical Risk Management, 2007, pp. 467-474, vol. 3, No. 3, Dove Medical Press Limited, eight pages.
Brooks, "Optimizing levodopa therapy for Parkinson's disease with levodopa/carbidopa/entacapone: implications from a clinical and patient perspective", Neuropsychiatric Disease and Treatment, 2008, pp. 39-47, vol. 4, No. 1, Dove Medical Press Limited, ten pages.
Berardelli et al, "Pathophysiology of Chorea and Bradykinesia in Huntington's Disease", Movement Disorders, 1999, pp. 398-403, vol. 14, No. 3, six pages.
Aryal et al, "Alteration of Striatal Tetrahydrobiopterin in Iron-Induced Unilateral Model of Parkinson's Disease", Korean J Physiol Pharmacol, Apr. 2014, pp. 129-134, vol. 18, seven pages.
International Search Report (PCT/ISA/210) issued in PCT Application No. PCT/US19/15143 dated Apr. 1, 2019 (four pages).
Written Opinion (PCT/ISA/237) issued in PCT Application No. PCT/US19/15143 dated Apr. 1, 2019 (14 pages).
"History of Changes for Study: NCT01127503, Metyrosine (Demser®) for the Treatment of Psychotic Disorders in Patients With Velocardiofacial Syndrome", NIH, U.S. National Library of Medicine, ClinicalTrials.gov archive, Sep. 28, 2011, three pages.
International Preliminary Report on Patentability (PCT/IB/326 & PCT/IB/373) issued in PCT Application No. PCT/US2019/015143 dated Aug. 13, 2020 (two pages).
Chinese-language Office Action issued in Chinese Application No. 201980010638.4 dated Dec. 21, 2022 with English translation (15 pages).
Ayd, F., "A Survey of Drug-Induced Extrapyramidal Reactions," J.A.M.A., Mar. 25, 1961, pp. 1054-1060, vol. 175, No. 12 (7 pages).
Brockmann, K. et al., "GBA-Associated Parkinson's Disease: Reduced Survival and More Rapid Progression in a Prospective Longitudinal Study", Movement Disorders, 2014, pp. 1-5, vol. 00, No. 00 (5 pages).

(56) References Cited

OTHER PUBLICATIONS

Data Sheet—Demser (Metyrosine), Valeant Pharmaceuticals North America LLC, Nov. 2015 (2 pages).
Data Sheet—Largactil, "Chemical structure of chlorpromazine hydrochloride", GLUv11 DSv7, Feb. 4, 2013, pp. 1-14 (14 pages).
Highlights of Prescribing Information—Clozaril (clozapine), Reference ID: 3676237, Sep. 2014, Novartis Pharmaceuticals Corporation, East Hanover, New Jersey 07936 (27 pages).
Engelman, K. et al., "Biochemical and Pharmacologic Effects of α-Methyltyrosine in Man", The Journal of Clinical Investigation, 1968, pp. 577-594, vol. 47 (18 pages).
Data Sheet—Haloperidol, American Health Packaging, Mar. 2020 (18 pages).
Leng, A. et al., "Effects of blocking the dopamine biosynthesis and of neurotoxic dopamine depletion with 1-methyl-4-phenyl-1,2,3,6-tetrahydropyridine (MPTP) on voluntary wheel running in mice", Behavioural Brain Research 154, Elsevier, (2004), pp. 375-383 (9 pages).
May, R. et al., "Parkinsonian Reactions Following Chlorpromazine and Reserpine", A. M. A. Archives of Neurology and Psychiatry, Department of Psychiatry, Ohio State University College of Medicine, Columbus Receiving Hospital and State Institute of Psychiatry, Jan. 5, 1956, pp. 522-524 (3 pages).
Highlights of Prescribing Information—Risperdal (risperidone), Ortho-McNeil-Janssen Pharmaceuticals, Inc., 2007, pp. 1-49 (49 pages).
Highlights of Prescribing Information—Seroquel, Reference ID: 3397413, Oct. 2013, AstraZeneca 2013, AstraZeneca Pharmaceuticals LP, Wilmington, DE 19850 (51 pages).
Shen, W., "A History of Antipsychotic Drug Development", Comprehensive Psychiatry, Official Journal of the American Psychopathological Association, Nov./Dec. 1999, pp. 407-414, vol. 40, No. 6 (8 pages).
Zigmond, M. et al., "Recovery of Feeding and Drinking by Rats after Intraventricular 6-Hydroxydopamine or Lateral Hypothalamic Lesions", Psychobiology Program, Departments of Biology and Psychology, University of Pittsburgh, Nov. 16, 1973, pp. 717-720 (4 pages).
Highlights of Prescribing Information—Risperdal Consta, 2007, Ortho-McNeil-Janssen Pharmaceuticals, Inc., pp. 1-50 (50 pages).

* cited by examiner

100 AMPT

102 AMPT methyl ester (hydrochloride)

110 aquayamycin 112 bulbocapnine 114 oudenone 116 3-iodotyrosine

120 L-tyrosine

122 L-phenylalanine

200

210

220

230

METHODS FOR DOPAMINE MODULATION IN HUMAN NEUROLOGIC DISEASES

CROSS REFERENCE TO RELATED APPLICATIONS

This application claims priority to and the benefit of U.S. Provisional Application Nos. 62/623,348, filed Jan. 29, 2018, and 62/650,813, filed Mar. 30, 2018, which are expressly incorporated herein by reference in their entirety.

FIELD OF INVENTION

The present invention is a novel method of treating Parkinson's Disease, Huntington's Disease and the like, diseases with abnormal dopamine-neurotransmission, using small molecules administered systemically that penetrate into the central nervous system to inhibit the rate-limiting step of dopamine synthesis in the central nervous system, the conversion of L-tyrosine to L-3, 4-dihydroxyphenylalanine (L-DOPA) by tyrosine hydroxylase along with its cofactors tetrahydrobiopterin and iron ($Fe^+$).

BACKGROUND

Abnormalities in dopamine neurotransmission underlie movement disorders, as exemplified by Parkinson's and Huntington's diseases.

Parkinson's disease manifests initially as a movement disorder, progressing from tremors to the combination of muscle rigidity and akinesia. Widespread neurologic impairment follows. The biologic hallmarks include loss of dopaminergic neurons in the brain (in the substantia nigra, largely in the pars compacta, within the basal ganglia) with protein accumulation (Lewy Bodies) and oxidative stress that impair function of the remaining cells (Fahn, S., Parkinsonism and Related Disorders The 200-year journey of Parkinson disease: Reflecting on the past and looking towards the future, *Parkinsonism Relat. Disord.* 46, 1-5 (2017), incorporated herein by reference in its entirety). With loss of these neuronal cell bodies, their axonal projections into the caudate nucleus and putamen of the midbrain are lost and/or lose their ability to synthesize and release dopamine.

The disease is the second most prevalent cause of neurologic degeneration and loss of independent function, affecting millions globally (National Institute for Health and Care Excellence, *Parkinson's Disease in Adults: Diagnosis and Management. NICE Guideline NG*71. (2017), incorporated herein by reference in its entirety).

This model of disease was reinforced in the 1970s with landmark Parkinson's studies demonstrating loss of dopaminergic neurons in the substantia nigra (Damier, P. et al., The substantia nigra of the human brain: II. Patterns of loss of dopamine-containing neurons in Parkinson's disease, *Brain* 122, 1437-1448 (1999), incorporated herein by reference in their entirety). that correlated with reduction in dopamine levels (Bernheimer et al., Brain Dopamine and the Syndromes of Parkinson, *J. Neurol. Sci.* 4, 145-148 (1973), incorporated herein by reference in its entirety). Post mortem studies linked these neurochemical abnormalities to motor dysfunction (Hartmann, A., Postmortem studies in Parkinson's disease, *Dialogues Clin. Neurosci.* 6, 281-293 (2004), Hirsch et al., Melanized dopaminergic neurons are differentially susceptible to degeneration in Parkinson's disease, *Nature* 334, 345-348 (1988), incorporated herein by reference in their entirety). Thus, medicines to increase dopamine levels in the caudate nucleus and putamen became the foundation of Parkinson's treatment, based on the rationale that pharmacologic levels of dopamine could reverse the akinesia and improve motor function (Fahn, S., Parkinsonism and Related Disorders The 200-year journey of Parkinson disease: Reflecting on the past and looking towards the future, *Parkinsonism Relat. Disord.* 46, 1-5 (2017); National Institute for Health and Care Excellence, *Parkinson's Disease in Adults: Diagnosis and Management. NICE Guideline NG*71. (2017), incorporated herein by reference in their entirety).

The current model of Parkinson's disease focuses on correcting the underlying dopamine deficiency in the midbrain, by providing additional dopamine or reducing its metabolism (National Institute for Health and Care Excellence. *Parkinson's Disease in Adults: Diagnosis and Management. NICE Guideline NG*71. (2017), incorporated herein by reference in its entirety), as well as by providing stimulation to the brain regions (electrically) that can stimulate these neural circuits to help relieve the movement disorder of Parkinson's disease (Bronstein et al., Deep brain stimulation for Parkinson disease an expert consensus and review of key issues, *Arch. Neurol.* 68, 165-171 (2011), incorporated herein by reference in its entirety). In addition, therapies focus on related complications, such as depression, fatigue, sleepiness, impulse disorders and loss of cognitive function, amongst others.

Thus the standard of care for Parkinson's—as recently summarized by the United Kingdom's NICE Treatment Guidelines—focused on providing dopaminergic support in the central nervous system, either by supplying dopamine or reducing its metabolic breakdown (National Institute for Health and Care Excellence. *Parkinson's Disease in Adults: Diagnosis and Management. NICE Guideline NG*71. (2017), incorporated herein by reference in its entirety). Clinical trials demonstrate such approaches are associated with improved motor function and independence in activities of daily living, though no clinical data show that any such therapy changes the underlying issues, natural history of, or the overall progression of the disease. In fact, these studies show that additional dopaminergic support for patients with Parkinson's disease may only be palliative (The Parkinson Study Group, Levodopa and the Progression of Parkinson's Disease, *N. Engl. J. Med.* 351, 2498-2508 (2004), incorporated herein by reference in its entirety). In parallel, the data show that whether patients are untreated or treated with standard of care, neurologic dysfunction progresses to cognitive impairment, psychiatric disorders and other systemic manifestations (National Institute for Health and Care Excellence. *Parkinson's Disease in Adults: Diagnosis and Management. NICE Guideline NG*71. (2017), incorporated herein by reference in its entirety).

Huntington's disease is caused by a genetic abnormality, typically presenting as a syndrome of abnormal, choreiform movements early in disease—also described as rapid, jerky, and repetitive involuntary movements—with late stage disease often featuring relative bradykinesia, though this descriptor captures only one of the signs/symptoms and is used herein to represent the late stage of disease. Current hypotheses include dopamine as a central contributor in a biphasic pattern, with early disease resulting from excess neurotransmission of dopamine and late stage from dopamine depletion (Cepeda, C. et al., The Role of Dopamine in Huntington's Disease, *Prog Brain Res* 211, 235-254 (2014), Chen, et al., Dopamine imbalance in Huntington's disease: A mechanism for the lack of behavioral flexibility, *Front. Neurosci.* 7, 1-14 (2013), incorporated herein by reference in their entirety).

Treatment of Huntington's rests largely on therapies that block dopamine neurotransmission across the synapse, doing so by inhibiting vesicular monoamine transporter (VMAT type 2). With impaired vesicular uptake of the presynaptic dopamine, these axons cannot release the dopamine into the intra-synaptic cleft. In addition to the effect of reducing choreiform movements however, presynaptic cytosolic dopamine is increased. Cytosolic dopamine is neurotoxic, and therefore, while its increase will negatively feedback on dopamine synthesis and lead to tissue-level dopamine depletion, the intended effect, antagonizing VMAT2 means that these presynaptic axons are exposed to dopamine toxicity. Such toxicity contributes to neuronal dysfunction and death, and either or both will shift the Huntington's patients from choreiform to bradykinetic state.

Therapeutics for Huntington's do not alter the natural history of the disease, and all rest on VMAT inhibition (Teva Pharmaceuticals USA. Austedo, Prod. Label (2017), Neurocrine Biosciences, Ingrezza (package insert), (2017), Valeant International Bermuda. *XENAZINE® (tetrabenazine) tablets, for oral use. Product Label* (2015), incorporated herein by reference in their entirety).

Preclinical data show that dopamine is toxic to dopaminergic neurons, and that reduction of its synthesis protects these cells from dysfunction and death. A novel approach is proposed herein, drug treatment(s) to reduce cellular dopamine production to protect neurons, and potentially restore proper dopamine control systems.

SUMMARY OF THE INVENTION

In accordance with the present invention, compositions and methods are provided that are effective in treating Parkinson's Disease and other diseases caused by reduced dopamine levels within neurons and/or abnormal dopamine-neurotransmission, exemplified by Huntington's Disease. These compositions are easily administered by different routes including oral and can be given in dosages that are safe and provide antagonistic behavior and/or effects to inhibit the production or uptake of dopamine.

This invention also relates to a correlation between a reduction in dopaminergic cells of the substantia nigra ($TH^+$ cells) and tissue dopamine.

In one embodiment, Parkinson's Disease and/or Huntington's Disease are treated using small molecules administered systemically that penetrate into the central nervous system to inhibit the rate-limiting step of dopamine synthesis in the central nervous system, the conversion of L-tyrosine to L-3,4-dihydroxyphenylalanine (L-DOPA) by tyrosine hydroxylase along with its cofactors tetrahydrobiopterin and iron ($Fe^+$).

Antagonism of tyrosine hydroxylase decreases levels of aminergic neurotransmitters, such as norepinephrine, epinephrine, and dopamine. One such tyrosine hydroxylase antagonist is metyrosine (U.S. Pat. Nos. 4,117,161, 2,868,818, Sjoerdsma, A. et al., Inhibition of Catecholamine Synthesis in Man with Alpha-Methyl-Tyrosine, and Inhibitor of Tyrosine Hydroxylase, *The Lancet* 286, 1092-1094 (1965), Engelman, K. et al., Metabolism of alpha-methyltyrosine in man: relationship to its potency as an inhibitor of catecholamine biosynthesis, *J. Clin. Invest.* 47, 568-576 (1968), incorporated herein by reference in their entirety). This and other therapies taught herein are synthesized and used in native form(s) as well as with deuterium substituting for hydrogen in one or more locations. To optimize patient compliance, many medicines are packaged in forms that delay the release of the active entity after oral administration.

In one embodiment of the present invention, a tyrosine hydroxylase inhibitor is administered as a treatment for Parkinson's disease and/or Parkinsonism and/or Huntington's disease.

In some embodiments of the present invention, a tyrosine hydroxylase inhibitor is administered as treatment of Parkinson's disease and/or Parkinsonism and/or Huntington's disease initially at a nominal dose that is gradually increased over days or weeks.

In some embodiments of the present invention, administration of a tyrosine hydroxylase inhibitor is administered as treatment of Parkinson's disease and/or Parkinsonism and/or Huntington's disease and supported by concomitant or intermittent administration of dopamine agonist therapy/therapies.

In some embodiments of the present invention, tyrosine hydroxylase activity is antagonized by administration of an inhibitor of tetrahydrobiopterin biosynthesis as treatment of Parkinson's disease and/or Parkinsonism and/or Huntington's disease.

In some embodiments of the present invention, a tyrosine hydroxylase inhibitor is administered with an inhibitor of tetrahydrobiopterin biosynthesis as treatment of Parkinson's disease and/or Parkinsonism and/or Huntington's disease.

In some embodiments of the present invention, a tyrosine hydroxylase inhibitor is administered with an inhibitor of tetrahydrobiopterin biosynthesis as treatment of Parkinson's disease and/or Parkinsonism and supported by concomitant or intermittent administration of dopamine agonist therapy/therapies.

In some embodiments of the present invention, a tyrosine hydroxylase inhibitor is administered with an inhibitor of tetrahydrobiopterin biosynthesis as treatment of Parkinson's disease and/or Parkinsonism and/or Huntington's disease and supported by concomitant or intermittent administration of VMAT2 inhibitor(s).

In some embodiments of the present invention, each of these treatment regimens is administered as a combination with any or all of a dopamine agonist, a monoamine oxidase type B (MAO-B) stimulator and catechol-O-methyltransferase (COMT) stimulator. In some embodiments of the present invention, each of these therapeutic molecules has one or more hydrogen atoms replaced with deuterium, strengthening the bond, slowing metabolism and improving pharmacokinetics and pharmacodynamics.

DETAILED DESCRIPTION

Figure 1:
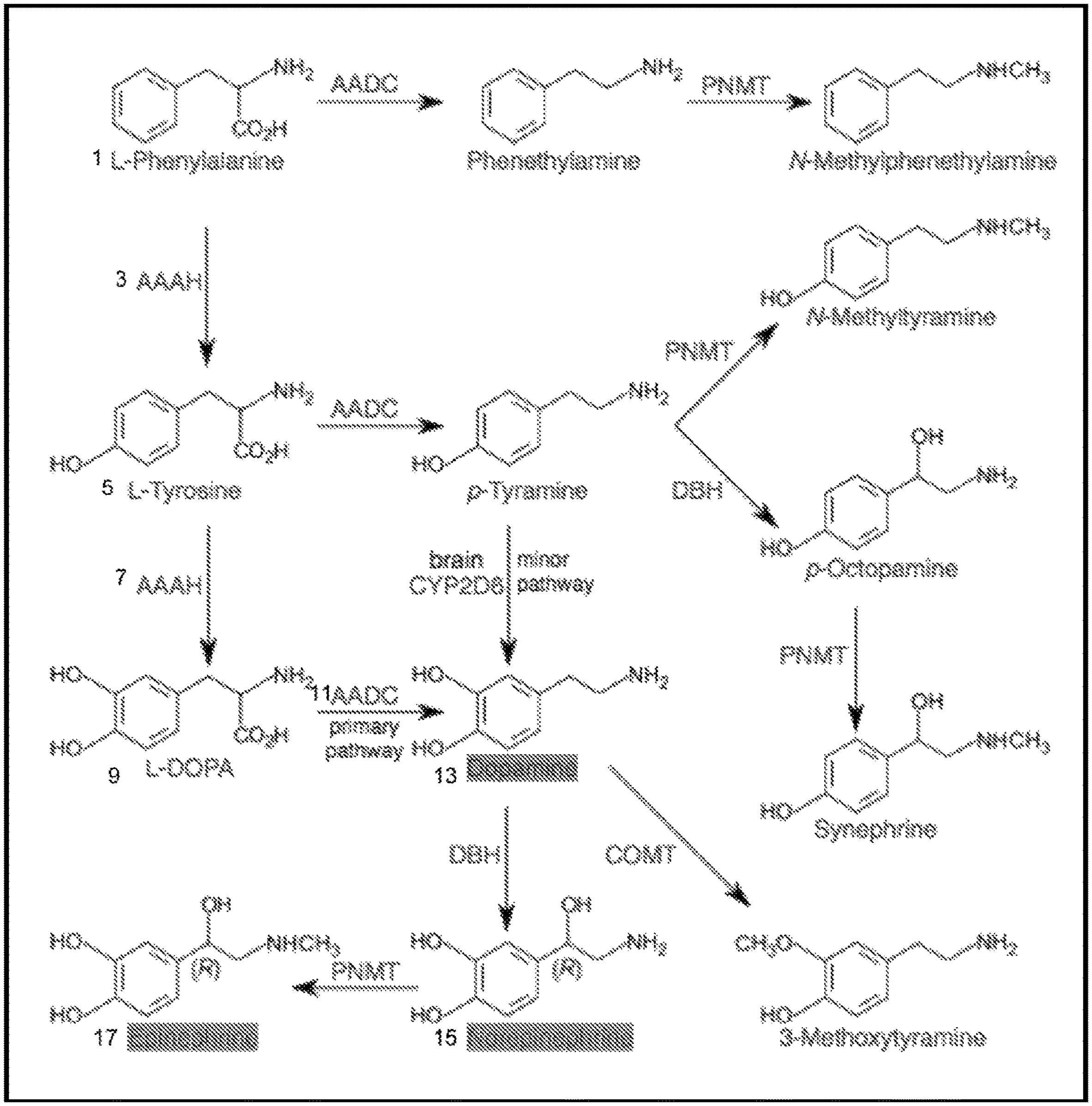
FIG. 1. Catecholamine biosynthesis from tyrosine (5) to L-dopa (9) via tyrosine hydroxylase (7), also known as aromatic amino acid hydroxylase, the rate-limiting step, and then to dopamine (13) via aromatic acid decarboxylase (11).
Figure 2:
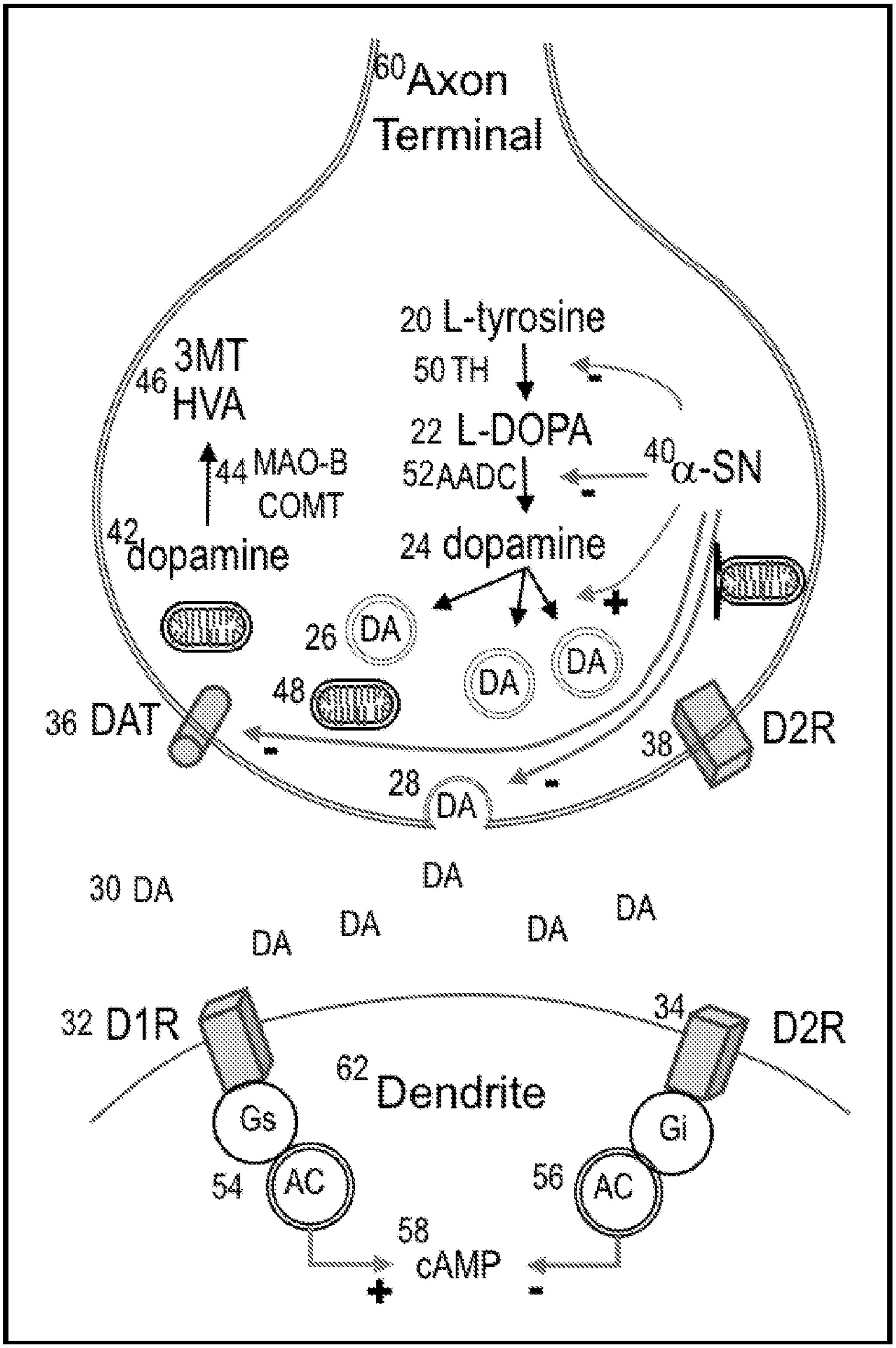
FIG. 2. Neurotransmission via dopaminergic pathway, from the pre-synaptic axon terminal (60) to the post-synaptic dendrite (62). Major synthetic, metabolic and feedback control mechanisms are represented.
Figure 3A:
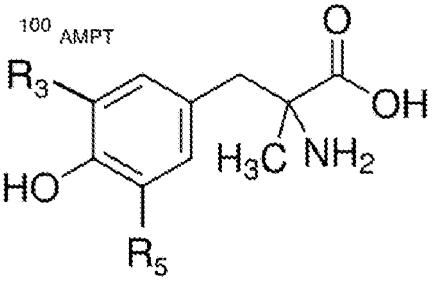
FIG. 3. Examples of chemicals used for direct inhibition of tyrosine hydroxylase, in FIG. 3(*a*) AMPT shown with a representative conjugate, the methyl ester form, in FIG. 3(*b*) alternative tyrosine hydroxylase inhibitors and in FIG. 3(*c*) template for side chain modification of the amino acid tyrosine hydroxylase inhibitors tyrosine and phenylalanine. For each and other embodiments taught herein, the R3 and R5 moieties undergo substitution with halides, either at R3 or at both locations, which increases potency as a tyrosine hydroxylase inhibitor. For embodiments based on these structures, methylation at RO increases potency. Substitutions by halides at R3 or R3 with R5 to form dihalides are additional embodiments of the invention.
Figure 3A:
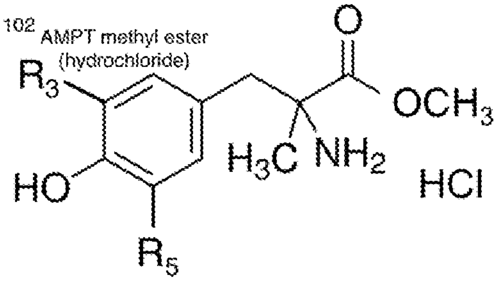
Figure 3B:
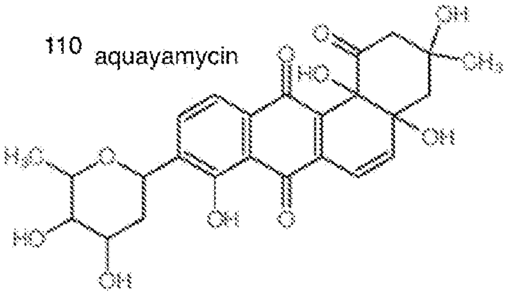
Figure 3B:
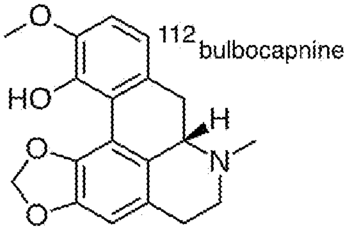
Figure 3B:
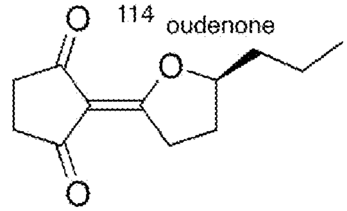
Figure 3B:
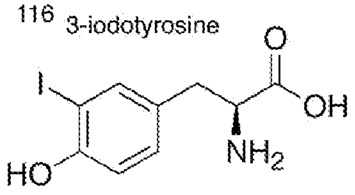
Figure 3C:
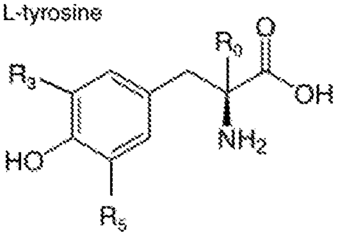
Figure 3C:
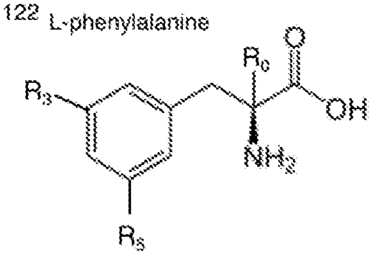

A biochemical hallmark of Parkinson's disease is loss of dopamine in the basal ganglia, particularly with loss of the dopaminergic neuronal cell bodies in the substantia nigra pars compacta (SNpc) (Damier, P. et al., The substantia nigra of the human brain: II. Patterns of loss of dopamine-containing neurons in Parkinson's disease, *Brain* 122, 1437-1448 (1999), Hirsch, E. et al., Melanized dopaminergic neurons are differentially susceptible to degeneration in Parkinson's disease, *Nature* 334, 345-348 (1988), incorporated herein by reference in their entirety). While symptomatic benefit results from administration of dopamine and dopaminergic therapies, such approaches do not appear to change the course of disease (The Parkinson Study Group, Levodopa and the Progression of Parkinson's Disease, *N. Engl. J. Med.* 351, 2498-2508 (2004), incorporated herein by reference in its entirety). As depicted in FIG. 2, dopaminergic neurotransmission from pre- to post-synaptic terminal is controlled on several levels. Pre-synaptic dopamine synthesis is controlled via effects on biopterin dependent enzyme tyrosine hydroxylase (50) conversion of tyrosine (20) to L-dopa (22). Dopamine (24) in the cytosol is sequestered within vesicles (26) based on VMAT2 activity, which prevents cellular toxicity. Upon stimulation, via membrane depolarization, vesicles fuse with the cell membrane (28) and dopamine is released into the synapse (30) via exocytosis. In addition to stimulating the post-synaptic membrane at D1 (32) and D2 (34) receptors, pre-synaptic D2 (38) receptors serve auto-regulatory function. The high levels of dopamine in the cleft result in rapid reuptake by the pre-synaptic terminal via DAT channels (36), with that dopamine stored once again in vesicles driven by VMAT2 activity, and free cytosolic dopamine (42) metabolized via MAO-B and COMT enzymes (44).

D1 and D2 receptors are G-protein coupled protein receptors (GCPR), with post-synaptic D1 (32) and D2 (34) receptors having opposing effects on dendritic cAMP (58) activity. D1 stimulation increases cAMP (58) via the stimulatory G protein coupled Gs-adenyl cyclase complex (54), and thereby intracellular calcium, while D2 stimulation reduces cAMP (58) via the inhibitory G protein coupled Gi-adenyl cyclase complex (56).

In a state of excess dopaminergic drive starting at the axon terminal, a deficit in VMAT2 driven vesicular storage exposes the axon to toxic free radicals formed from breakdown of cytosolic dopamine. The protein α-synuclein (40) is known to be the major component of intracellular Lewy Bodies, which serve as markers of disease progression as well as impairing neuronal function. In addition, α-synuclein appears to play several roles in mitigation of the risk of dopamine toxicity within the axon terminal, including (a) inhibition of tyrosine hydroxylase (50) and amino acid decarboxylase (52), (b) stimulating formation of vesicles for dopamine storage (26) and reducing the rate of DAT-mediated dopamine reuptake (36). α-synuclein also spares dendritic exposure to dopamine, as it blunts vesicular exocytosis of dopamine (28). In addition, binding between α-synuclein and free cytosolic dopamine leads to reduced cellular exposure to dopaminergic free radicals, though at the cost of protofibril formation that hastens the development of Lewy Bodies. These mechanistic phenomena suggest that Lewy Body formation may represent protective neuronal mechanisms for brief exposure to toxic dopamine that result in additional pathologic effects when the mechanism remains active long-term.

VMAT2 deficiency whether due to genetic abnormality or altered gene expression further exposes the neuron and its axon to dopamine toxicity. When dopamine is stored within the axonal vesicles, as it would be prior to exocytosis into the intrasynaptic cleft, it is protected against oxidation. And that oxidation of dopamine is a major trigger leading to neuronal toxicity. As described below, while total dopamine is markedly depleted, the per cell amount of dopamine is near normal in Parkinson's disease. Thus, the VMAT2 deficiency of Parkinson's means that the balance between vesicular and cytosolic dopamine shifts towards super-normal cytosolic dopamine content, amplifying the amount of oxidized dopamine and the risk of cellular and organelle (e.g., mitochondrial) dysfunction and death from this toxic form of dopamine (Lohr, K. M. & Miller, G. W., VMAT2 and Parkinson's disease: harnessing the dopamine vesicle, *Expert Rev. Neurother.* 14, 1115-1117 (2014), incorporated herein by reference in its entirety). The physiology is similar for Huntington's disease patients treated with VMAT2 inhibitor(s). To prepare dopamine for synaptic release, VMAT2 mediates its storage within axonal vesicles (26). Without that process, dopamine remains free within the cytosol of the axon (60) where it oxidizes a range of cellular targets and cannot be released. That oxidative stress contributes to cell dysfunction and death (Bernheimer et al., Brain Dopamine and the Syndromes of Parkinson, *J. Neurol. Sci.* 4, 145-148 (1973), incorporated herein by reference in its entirety). While the VMAT2 inhibitor(s) protects the post-synaptic dendrite (62) from excess dopamine, it leads to loss of pre-synaptic function. Such is a hallmark of late stage Huntington's disease.

In untreated Huntington's disease, the pathophysiology starts with excess dopaminergic activity, which is responsible for the choreiform movements and with that chronic state, leads to the pre-synaptic axon function and viability adversely affected by dopamine-mediated toxicity. Reduction of dopamine synthesis is taught herein as a novel means to alter the natural history of disease and the symptomatic manifestations.

Current approaches resting on VMAT2 inhibition protect the post-synaptic dendrites from toxicity and reduce choreiform movements. However, this puts the presynaptic machinery at risk. Thus, taught herein is a novel approach of blocking dopamine synthesis without compromising the ability to store those smaller amounts of dopamine within the vesicles.

The complexity and risk from these control mechanisms are underscored by recognition that the polymers deposited in mitochondrial impair energy production, further amplifying oxidative stress. Directly and/or indirectly, alpha-synuclein impairs neuronal function and increases likelihood of cell death.

To date, the precise trigger(s) for the development of sporadic Parkinson's Disease is(are) unknown, though several genetic forms lead to similar pathology, with dopamine associated toxicity along with reduced dopamine stores resulting from loss of dopaminergic neurons. Thus, the genetic forms also are treated as a dopamine deficiency state that must be reversed. This invention teaches a novel method for treating Parkinson's disease in both subclinical and clinical states, reducing dopamine production and/or increasing its metabolism within viable neurons.

Currently, the genetic basis for Huntington's Disease is known, though the shift from the early choreiform to the late bradykinetic state is associated with loss of dopaminergic neurons (Bernheimer et al., Brain Dopamine and the Syndromes of Parkinson, *J. Neurol. Sci.* 4, 145-148 (1973), incorporated herein by reference in its entirety). Neurotoxicity from free cytosolic dopamine is a driver of that shift in cell population—both in untreated disease and VMAT2 inhibitor treated disease. Thus, this invention teaches a novel method for treating Huntington's disease in both early and late clinical states, reducing dopamine production and/or increasing its metabolism within viable neurons.

Disclosed herein are methods for reducing dopamine in the neurons of the central nervous system, in particular for neurons within the substantia nigra pars compacta, as a treatment for patients with Parkinson's Disease, including those identified with neurochemical abnormalities that would be expected to evolve into overt Parkinson's Disease, as well as for patients with Huntington's Disease, whether early or late in disease evolution, to slow, reverse and/or halt disease progression.

Based on metabolism of dopamine, the approaches could include any or all of the following: antagonism of tyrosine hydroxylase activity, antagonism of amino acid decarboxylase, stimulation of monoamine oxidase type B activity and/or stimulation of catechol-O-methyltransferase activity. Because the amino acid decarboxylase relevant to Parkinson's disease and/or Parkinsonism and/or Huntington's disease—dopamine decarboxylase—is not rate limiting in dopamine synthesis, this is not a focus of this invention. Therefore, taught herein are methods that antagonize tyrosine hydroxylase, using direct enzymatic inhibitors as well as using direct inhibitors of its required co-factor, tetrahydrobiopterin.

While total dopamine amounts are depleted, on a per cell basis Parkinson's disease and Huntington's disease patients appear to maintain normal amounts of dopamine synthesis. However, neurons cannot protect themselves from dopamine toxicity even at these normal physiologic levels, and therefore, would appear to be at heightened risk of toxicity from the pharmacologic levels produced by medicines (Meiser et al., Complexity of dopamine metabolism. *Cell Commun. Signal.* 11, 1-18 (2013), Moon, H. E. & Paek, S. H. Mitochondrial Dysfunction in Parkinson's Disease, *Exp. Neurobiol.* 24, 103-16 (2015), incorporated herein by reference in their entirety). With increase amount of alpha-synuclein, Parkinson's neurons can no longer protect themselves from dopamine toxicity by sequestering it within intracellular vesicles (Perez, R. G. et al., A role for α-Synuclein in the Regulation of Dopamine Biosynthesis, *J. Neurosci.* 22, 3090-3099 (2002), Venda et al., α-Synuclein and dopamine at the crossroads of Parkinson's disease, *Trends Neurosci.* 33, 559-568 (2010), incorporated herein by reference in their entirety). And because they suffer from mitochondrial dysfunction, the cells are exposed to oxidative stress (free radical generation) that impairs cellular function (Moon, H. E. & Paek, S. H., Mitochondrial Dysfunction in Parkinson's Disease, *Exp. Neurobiol.* 24, 103-16 (2015), incorporated herein by reference in its entirety). In the presence of dopamine, this oxidative stress results in formation of alpha-synuclein protofibrils (Conway, K. A., Kinetic Stabilization of the alpha-Synuclein Protofibril by a Dopamine-alpha-Synuclein Adduct, *Science* 294, 1346-1349 (2001), incorporated herein by reference in its entirety). Formation of Lewy Bodies further impairs cellular function (Perez, R. G. et al, A role for α-Synuclein in the Regulation of Dopamine Biosynthesis, *J. Neurosci.* 22, 3090-3099 (2002), Venda et al., α-Synuclein and dopamine at the crossroads of Parkinson's disease, *Trends Neurosci.* 33, 559-568 (2010), incorporated herein by reference in their entirety). Pharmacologic treatment of Huntington's inhibits VMAT2, which reduces the capacity to store dopamine within vesicles and similar to in Parkinson's, results in a relative excess of dopamine in the neurons. These factors contribute to cell death (Ogawa et al., L-DOPA treatment from the viewpoint of neuroprotection: Possible mechanism of specific and progressive dopaminergic neuronal death in Parkinson's disease, *J. Neurol.* 252, 23-31 (2005), incorporated herein by reference in its entirety).

Tyrosine hydroxylase, with its four isoforms, is the rate limiting enzyme in the synthesis of dopamine in the central nervous system (Meiser et al., Complexity of dopamine metabolism, *Cell Commun. Signal.* 11, 1-18 (2013), Levitt, et al., Elucidation of the Rate-Limiting Step in Norepinephrine Biosynthesis in the Perfused Guinea-Pig Heart, *J. Pharmacol. Exp. Ther.* 148, 1-8 (1965), incorporated herein by reference in their entirety), working with its cofactor tetrahydrobiopterin.

In one embodiment, the treatment is the tyrosine hydroxylase inhibitor metyrosine (Demser®, manufactured as the L-enantiomer), also known as alpha-methyl-p-tyrosine (AMPT).

In another embodiment, the treatment is a racemic mixture of alpha-methyl-p-tyrosine.

In another embodiment, due to risk of nephrolithiasis during AMPT use, a combination of AMPT with a urinary alkalinizing agent is administered.

AMPT antagonizes tyrosine hydroxylase (Sjoerdsma et al., Inhibition of Catecholamine Synthesis in Man with Alpha-Methyl-Tyrosine, and Inhibitor of Tyrosine Hydroxylase, *The Lancet* 286, 1092-1094 (1965), Engelman et al., Metabolism of alpha-methyltyrosine in man: relationship to its potency as an inhibitor of catecholamine biosynthesis, *J. Clin. Invest.* 47, 568-576 (1968), Nagatsu et al., Tyrosine Hydroxylase: The Initial Step in Norepinephrine Biosynthesis, *J. Biol. Chem.* 239, 2910-2917 (1964), Udenfriend et al., Inhibitors of Purified Beef Adrenal Tyrosine Hydroxylase, *Biochem Pharmacol* 14, 837-845 (1965), incorporated herein by reference in their entirety). An AMPT concentration of $10^{-4}$M inhibits tyrosine hydroxylase by 86% in guinea pig brain particle preparations and by 50% at concentrations of $2.5\times10^{-5}$ M in bovine adrenal gland preparations (Nagatsu et al., Tyrosine Hydroxylase: The Initial Step in Norepinephrine Biosynthesis, *J. Biol. Chem.* 239, 2910-2917 (1964), Udenfriend et al., Inhibitors of Purified Beef Adrenal Tyrosine Hydroxylase, *Biochem Pharmacol* 14, 837-845 (1965), incorporated herein by reference in their entirety). Various additional dosage forms and concentrations of AMPT are also effective, ranging between 500-2500 mg/day.

Additional compounds represent other embodiments of the invention taught, based on data that establish their potency as inhibitors of tyrosine hydroxylase.

Each of these listed compounds in Tables 1A and 1B (shown below) are embodiments of the current invention. (See, Nagatsu et al., Tyrosine Hydroxylase: The Initial Step in Norepinephrine Biosynthesis, *J. Biol. Chem.* 239, 2910-2917 (1964), Udenfriend et al., Inhibitors of Purified Beef Adrenal Tyrosine Hydroxylase, *Biochem Pharmacol* 14, 837-845 (1965), incorporated herein by reference in their entirety).

TABLE 1A

Amino acid analogs inhibiting tyrosine hydroxylase

| Compound | Concentration for 50% Inhibition (M) | Concentration (M) | % Inhibition |
|---|---|---|---|
| L-tryptophan | >1 × $10^{-3}$ | $10^{-4}$ | 50 |
| D-tryptophan | | $10^{-4}$ | 0 |
| L-phenylalanine | 2 × $10^{-4}$ | $10^{-4}$ | 78 |
| D-phenylalanine | >1 × $10^{-3}$ | $10^{-4}$ | 7 |
| DL-p-fluoro-phenylalanine | | $10^{-4}$ | 61 |
| 3-iodo-L-tyrosine | 5 × $10^{-7}$ | | |
| 3-chloro-L-tyrosine | 1 × $10^{-5}$ | | |
| 3-fluoro-DL-tyrosine | 1 × $10^{-3}$ | | |
| 3,5-diiodo-L-tyrosine | 2 × $10^{-5}$ | | |
| 3,5-dibromo -L-tyrosine | 5 × $10^{-4}$ | | |
| α-methyl-L-tyrosine | 2.5 × $10^{-5}$ | $10^{-4}$ | 86 |
| α-methyl-D-tyrosine | >1 × $10^{-3}$ | | |
| α-methyl-m-DL-tyrosine | >1 × $10^{-3}$ | 2 × 10–4 | 92 |
| α-methyl-DL-phenylalanine | 8 × $10^{-5}$ | | |
| 3-iodo-α-methyl-DL-tyrosine | 3 × $10^{-7}$ | | |
| 3-bromo-α-methyl-DL-tyrosine | 1.5 × $10^{-6}$ | | |
| 3-chloro-α-methyl-DL-tyrosine | 5 × $10^{-6}$ | | |
| 3-fluoro-α-methyl-DL-tyrosine | 2 × $10^{-4}$ | | |
| 3-chloro-4-methoxy-α-methyl-DL-phenylalanine | 5 × $10^{-4}$ | | |

TABLE 1B

Catecholamine analogs inhibiting tyrosine hydroxylase

| Compound | Concentration for 50% Inhibition (M) | Concentration (M) | % Inhibition |
|---|---|---|---|
| dopamine | | $10^{-4}$ | 56 |
| L-norepinephrine | 1 × $10^{-3}$ | | |
| DL-norepinephrine | | 2 × $10^{-4}$ | 53 |
| L-dopa | | $10^{-4}$ | 68 |
| D-dopa | | $10^{-4}$ | 0 |
| L-epinephrine | | $10^{-4}$ | 35 |
| D-epinephrine | | $10^{-4}$ | 47 |
| 3,4-dihydroxyphenyl-acetamide | 1 × $10^{-3}$ | | |
| 3,4-dihydroxyphenyl-propyl-acetamide (H-22/54) | 2 × $10^{-5}$ | $10^{-4}$ | 84 |
| 3,4-hydroxy-L-phenylalanine | 2 × $10^{-3}$ | | |
| 3,4-hydroxy-D-phenylalanine | >4 × $10^{-3}$ | | |
| α-methyl-3,4-dhydroxy-L-phenylalanine (Aldomet) | 1.5 × $10^{-3}$ | | |
| α-methyl-3,4-dhydroxy-D-phenylalanine | >8 × $10^{-3}$ | | |

Amino acid derivatives also act as tyrosine hydroxylase inhibitors (Udenfriend et al., Inhibitors of Purified Beef Adrenal Tyrosine Hydroxylase, *Biochem Pharmacol* 14, 837-845 (1965), incorporated herein by reference in its entirety). For example, because most analogs of phenylalanine and tyrosine inhibit tyrosine hydroxylase, embodiments include any such analog, embodiments include racemic or L-amino acid in particular. Additional potency results from α-methylation, and thus such compounds are taught herein as embodiments. Substitution at the 3-position of the benzene ring of relevant amino acids with a halogen atom adds potency, and such compounds are taught herein as additional embodiments. Substitution at both the 3 and 5 positions with halogen atoms are taught herein as additional embodiments of this invention.

Hoffman, incorporated herein by reference, describes several families of tyrosine hydroxylase inhibitors, though in the setting of cancer and not neurologic therapeutics (U.S. Patent Publication No. 2017/0056371, incorporated herein by reference in its entirety). These compounds are additional embodiments of the invention taught herein, and include: one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl)methoxy]phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl)

propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I2)-oSu, Fmoc-tyr(3-$NO_2$)—OH, α-methyl-L-tyrosine, α-methyl-D-tyrosine, and α-methyl-DL-tyrosine. Taught herein are dose ranges from 1 μg to 25 g per day for each of these compounds.

Additional embodiments of the invention use alternative tyrosine hydroxylase inhibitors. (See, Table 2).

TABLE 2

Tyrosine hydroxylase inhibitors taught herein as therapies for Parkinson's disease and/or Parkinsonism substituted for alpha-methyl-p-tyrosine.

| Chemical | Formula | Molar Mass | Highest Prior Dose | Max Dose Herein |
|---|---|---|---|---|
| 3-iodotyrosine[1] | $C_9H_{10}INO_3$ | 307.09 g/mol | — | — |
| bulbocapnine | $C_{19}H_{19}NO_4$ | 325.36 g/mol | ~200 mg/d | 2 mg/d |
| aquayamycin[2] | $C_{25}H_{26}O_{10}$ | 486.47 g/mol | — | 60 mg/d |
| oudenone | $C_{12}H_{16}O_3$ | 208.25 g/mol | ~1 g/d | 10 g/d |

[1]3-Iodotyrosine is an intermediate in the synthesis of thyroid hormones and its effects systemically preclude its delivery in this manner for the intended central nervous system effect.
[2]The LD 50 in mice is reported at a dose as low as 12.5 mg/kg, the human equivalent of 1 mg/kg in 60 kg adult, which is therefore expected to be the maximum dose for this invention.

Oudenone is a pentene based molecule identified from a needle-leaf tree demonstrated to inhibit tyrosine hydroxylase when directly measured, and also reduce blood pressure in spontaneously hypertensive rats (Umezawa, H. et al. A New Microbial Product, Oudenone, Inhibiting Tyrosine Hydroxylase, *J. Antibiot.* (Tokyo) 23, 514-518 (1970), incorporated herein by reference in its entirety). These investigators prepared sodium, potassium, calcium, magnesium and barium salts. Additional embodiments include use of aquayamycin as a tyrosine hydroxylase inhibitor, with potency near that reported for 3-iodo-α-methyl-DL-tyrosine (Udenfriend et al., Inhibitors of Purified Beef Adrenal Tyrosine Hydroxylase, *Biochem Pharmacol* 14, 837-845 (1965), Ayukawa, S. et al. Inhibition of Tyrosine Hydroxylase by Aquayamycin, *J. Antibiot.* (Tokyo) 21, 350-353 (1968), incorporated herein by reference in their entirety). Taught herein are dose ranges from 1 μg to 25 g per day for each of these compounds.

As taught for oudenone, each of the embodiments taught herein are administered as any of such salt forms.

Another embodiment impairs biosynthesis of tetrahydrobiopterin via sulfa compounds that cross the blood-brain-barrier, requisite for affecting tyrosine hydroxylase catalyzed dopamine production. Embodiments include sulfathiazole, sulfamethoxazole, sulfadiazine, sulfapyridine and sulfamethazine, each of which inhibits sepiapterin reductase, which catalyzes the final step in tetrahydrobiopterin synthesis, with IC50 values below 100 nM (Haruki et al., Tetrahydrobiopterin biosynthesis as an off-target of sulfa drugs, *Science* 340, 987-991 (2013), incorporated herein by reference in its entirety). Examples of such embodiments are provided in Table 3, where for each, one embodiment is to start at low dose and titrate up to target or maximally tolerated dose, as exemplified for alpha-methyl-p-tyrosine in Table 4.

TABLE 3

Examples of tyrosine hydroxylase inhibitors as replacements for alpha-methyl-p-tyrosine in example embodiments of the invention with maximum daily doses to be used

| Chemical | Highest Prior Dose | Max Dose Herein |
|---|---|---|
| sulfathiazole[1] | 1.5 gm/d | 1.5 gm/d |
| sulfamethoxazole | 1.6 gm/d | 16 gm/d |
| sulfadiazine | 4 g/day | 40 g/day |
| sulfapyridine[2] | 16 g/day (sulfasalazine) | 160 g/d (sulfasalazine) |
| sulfamethazine[3] | only used in large animals | — |

[1]Sulfathiazole is not administered at dose higher than previously used as any higher produces unacceptable side effect profile.
[2]Sulfapyridine human exposure results from metabolism of sulfasalazine, which is given at doses up to 16 g/day and an embodiment uses this dosing form for the intended effect.
[3]Sulfamethazine is only used in animals with max dose of 250 mg/kg, the equivalent of approximately 17 kg/day, indicating this compound is not viable as human therapeutic.

TABLE 4 alpha-methyl-p-tyrosine dosing schedule

| Visit | Dosing (mg) | Daily Dose (mg) |
|---|---|---|
| Week 1: | 25/25 | 50 |
| Week 2: | 50/50 | 100 |
| Week 3: | 100/100 | 200 |
| Week 4: | 100/100/100 | 300 |
| Week 5: | 150/150/150 | 450 |
| Week 6: | 200/200/200 | 600 |
| Week 7: | 250/250/250 | 750 |
| Week 8: | 300/300/300 | 900 |
| Week 9: | 400/400/400 | 1200 |
| Week 10: | 500/500/500 | 1500 |

One of the effects of methotrexate is inhibition of dihydropteridine reductase (DHPR), an enzyme critical for formation of tetrahydrobiopterin, the cofactor required for tyrosine hydroxylase inhibition. Thus another embodiment is use of methotrexate to inhibit tyrosine hydroxylase activity indirectly.

Another embodiment is administering the target dose as the starting dose. For the embodiments that use any of these sulfa compounds, dosing starts as recommended in approved labeling from the U.S. Food and Drug Administration, with maximum doses an order of magnitude higher than specified for primary indications and/or prior pharmacology studies, with limitations noted in Tables 2 and 3.

Alpha-methyl-p-tyrosine can be dosed between κ mg a day up to 2000 mg per day. Taught herein is the method of initiating therapy at low doses that are gradually increased, over days, weeks or months.

In one embodiment, doses start at a range of 1 mg daily up to 250 mg daily would be the starting dose, and target dose would range from 100 mg daily to 1000 grams daily. Table 4 is merely one example of how a dose titration is completed, in this case of a patient started at 50 mg daily and titrated to 1500 mg daily.

In another embodiment, doses start at frequencies of administration less than four times daily, including formulations up to once monthly via depo methods, where depo refers to pharmaceutical method of injecting or implanting a therapeutic agent into a tissue where it is absorbed more slowly for prolonged maintenance of therapeutic drug levels in the body. In another embodiment, the amount of each dose is increased and in another embodiment, the frequency of doses is increased, in order to increase the total daily dosage.

In another embodiment, the amount of each dose and the frequency of dosing are both used to increase the total daily drug dose. One of the ways to explain this embodiment is shown in Table 4, using alpha-methyl-p-tyrosine as the example, provided to show only one representation of a dose titration schedule and one example of a tyrosine hydroxylase antagonist. Other tyrosine hydroxylase antagonists and doses would be known to a person of ordinary skill in the art.

In another embodiment, the tyrosine hydroxylase inhibitor is administered using this graduated dosing approach while continuing the background therapy including dopaminergic medicines, including but not limited to levodopa-containing agents, MAO-B inhibitors and/or COMT inhibitors, as well as dopamine agonists. For this embodiment, the dose(s) of the background medicine(s) are gradually reduced while the tyrosine hydroxylase inhibitor dose is increased or while the dose of tyrosine hydroxylase inhibitor is held constant.

In another embodiment, the standard dopaminergic therapies are discontinued prior to initiation of therapy with tyrosine hydroxylase inhibition.

In another embodiment, the standard dopaminergic therapies are introduced as clinically required to help the patient(s) tolerate the increase in the dose of tyrosine hydroxylase inhibitor.

In another embodiment, the standard dopaminergic therapies are re-introduced or the dose(s) augmented as required to stabilize patient(s) clinically during the introduction and dose-titration of the tyrosine hydroxylase inhibitor(s) for a finite period of time.

In another embodiment, the use of deep brain stimulation is reduced to the minimum required for clinical stability, with the stimulation used more or less as clinically indicated, and in some embodiments, withdrawn (even if not explanted).

In another embodiment, the tyrosine hydroxylase and/or tetrahydrobiopterin inhibitor(s) is(are) manufactured in modified release formulation(s) to reduce dosing frequency and/or control drug levels.

In some embodiments, diffusion systems are used, including use of polymer coatings that reduce the rate of dissolution following ingestion.

In some embodiments, active drugs are dissolved in a gelling agent.

In some embodiments, active drug(s) are administered in tablet(s) coated with semi-permeable membrane or laser-drilled holes, through either of which drug release follows the absorption of water while passing through the gastrointestinal system.

In some embodiments, active drug(s) are manufactured within a matrix composed of polymers or lipids with delayed erosion by digestive enzymes.

In some embodiments, active drug(s) are manufactured as liquids or liquid suspensions and administered intra-nasally, with starting doses then as low as 1/10 to 1/1,000 of those listed herein.

In some embodiments, the tyrosine hydroxylase inhibitor is administered as its salt, ester, acid, gluconate, carbonate, anhydrous or free base forms.

In other embodiments, the tyrosine hydroxylase inhibitor is substituted with other known tyrosine hydroxylase inhibitors, none of which are described to date as treatments of Parkinson's disease or Parkinsonism in Tables 1 and 2.

In other embodiments, tyrosine hydroxylase activity is inhibited indirectly via inhibition of tetrahydrobiopterin (Table 3) administered in conjunction with direct tyrosine inhibitor(s).

In one such test, Parkinson's patients will be treated with one or more, in combination of succession, of the compounds taught herein for this use. Such a clinical trial will include both those patients early in the disease, not yet treated with pharmacologic stimulators of dopamine, as well as those already receiving such agents. Regulators may request such studies to be conducted separately on each population.

In such or any other clinical trials, standard measures of clinical status may be used to assess outcome, such as the Unified Parkinson's Disease Rating Scale. Functional tests evaluating ambulation are also useful outcomes for measurement, such as the 6 minute walk test, timed up and go test, and the like. Imaging of brain function, such as via PET or SPECT scanning, and the like, are used for understanding mechanisms of drug effect, and may be used in clinical testing. Other such functional tests would be known to a person of ordinary skill in the art.

In other embodiments, Huntington's patients are treated with the tyrosine hydroxylate inhibitor(s) and/or tetrahydrobiopterin inhibitor with VMAT2 inhibitor(s) during a transition from VMAT2 inhibition.

In Parkinson's disease, treatment to increase dopaminergic levels is associated with adverse effects exemplified by tardive dyskinesia. This is often associated with peak drug levels. In the same patient(s), as the dopamine and/or drug levels wane, the tardive dyskinesia is replaced by akinesia or bradykinesia, referred to as "off periods." A focus of drug developers is levodopa-based therapies that produce more favorable pharmacokinetics to reduce these swings, as well as permit less frequent dosing.

Taught herein is deuteration of the therapies. Timmins and others teach how deuterium's heavier molecular weight increases the strength of its bonds compared to hydrogen atom(s). With that greater strength comes slower metabolism, longer half-life and less variability in drug levels (Timmins, G. S. HHS Public Access, *Expert Opin Ther Pat* 24(10), 1067-1075 (2014), Gant, T. G. & Shahbaz, M. M., Benzoquinoline Inhibitors of Vesicular Monoamine Transporter 2. (2013), (73), Sommer, A. et al., Formulations Pharmacokinetics of Deuterated Benzoquinoline Inhibitors of Vesicular Monoamine Transporter 2. (2016), incorporated herein by reference in their entirety). Such changes in pharmacokinetics are advantageous in clinical practice and taught herein for Parkinson's, Huntington's and other diseases/disorders with altered dopamine metabolism treated with tyrosine hydroxylase inhibition.

Figure 4:
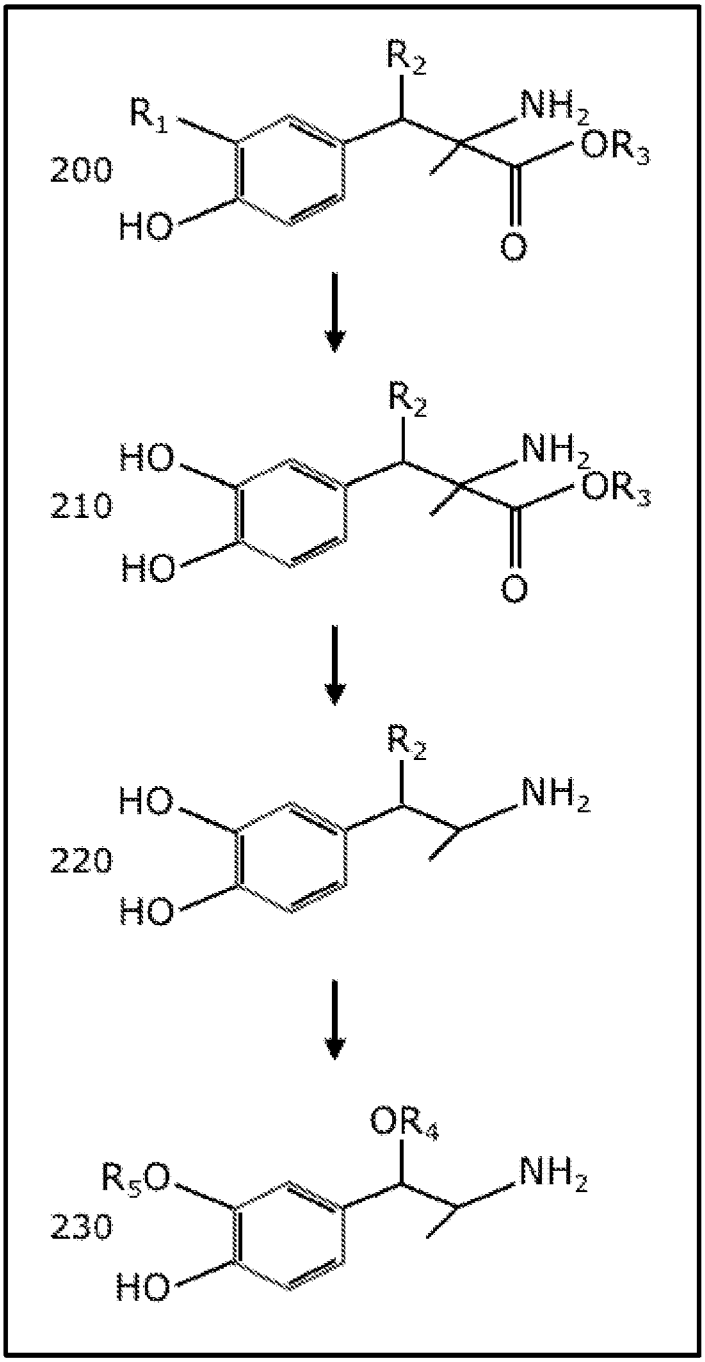
FIG. 4. Primary human metabolic pathway of alpha-methyl-p-tyrosine with exemplary deuteration sites.
Figure 5:
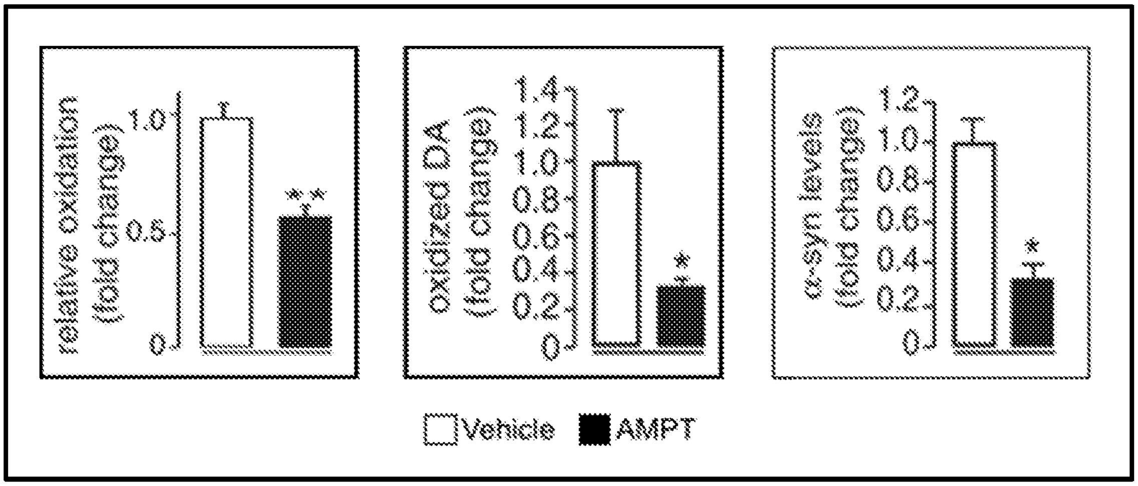
FIG. 5. Effect of chronic inhibition of dopamine synthesis with AMPT in dopaminergic iPS cells originating from DJ-1 homozygous Parkinson's patients treated with AMPT showing reduced oxidative stress, lower levels of oxidized dopamine, and blunted deposition of α-synuclein.

The method of deuteration is taught herein, using AMPT as an example, with its metabolic pathway shown in FIG. 4. Examples of deuteration target(s) for alpha-methyl-p-tyrosine (AMPT), shown as the metabolic pathway of AMPT in humans. Each R represents the site of a hydrogen atom in non-deuterated state, as well as a site for deuteration to inhibit the rate of metabolism from one step to the next. 200: alpha-methyl-p-tyrosine (AMPT), 210: alpha-methyl-dopa (AMD), 220): alpha-methyl-dopamine (AMDA), 230: alpha-methyl-norepinephrine (AMNE). AMPT (200) is metabolized to alpha-methyl-dopa (210) then to alpha-methyl-dopamine (220) and finally to alpha-methyl-norepinephrine (230) (Engelman et al., Metabolism of alpha-methyltyrosine in man: relationship to its potency as an inhibitor of catecholamine biosynthesis, *J. Clin. Invest.* 47, 568-576 (1968), Brogden et al., alpha-Methyl-p-Tyrosine: A Review of its Pharmacology and Clinical Use, *Drugs* 21, 81-89 (1981), incorporated herein by reference in their entirety). Delivered orally, the drug is well absorbed (~69%) (Brogden et al., alpha-Methyl-p-Tyrosine: A Review of its Pharmacology and Clinical Use, *Drugs* 21, 81-89 (1981), incorporated herein by reference in its entirety) and relatively little of these metabolites are recovered in the urine. Trace amounts of each can be detected (Engelman et al., Metabolism of alpha-methyltyrosine in man: relationship to its potency as an inhibitor of catecholamine biosynthesis, *J. Clin. Invest.* 47, 568-576 (1968), incorporated herein by reference in its entirety).

In FIG. 4, locations for deuteration are indicated by $R_n$, which are occupied by hydrogen atoms in native state. Taught herein is substitution at one or more of the $R_n$ locations with a deuterium atom in place of a hydrogen atom. Deuteration results in stronger bonds and therefore slower reactions at that/those bond(s). Included is substation at $R_5$ in alpha-methyl-norepinephrine, as dehydroxylation at $OR_5$ produces trace amounts of alpha-methyl-tyramine.

Because Parkinson's and Parkinsonism feature presynaptic axonal cytosolic dopamine levels that are neurotoxic, whether the cause is due to one or more of the known or unknown genetic causes, or the disease is idiopathic in etiology, the therapeutics taught herein are applicable to genetic or non-genetic causes, including as examples GBA, LRRK2, SNCA, VPS35, Parkin, PINK1, and DJ1.

A person of ordinary skill in the art would understand that modifications and substitutions could be made to the invention disclosed herein, as relates to the compounds, methods of use and means for measuring the clinical effects.

What is claimed is:

1. Methods of treating Parkinson's disease and/or Parkinsonism by antagonizing tyrosine hydroxylase via administering to a human patient in need thereof, a composition comprising one or more of the competitive inhibitors of tyrosine hydroxylase including alpha-methyl-p-tyrosine, wherein the alpha-methyl-p-tyrosine is administered at a nominal dose or doses and then administered in a therapeutic dose or doses that are gradually increased over days or weeks.

2. The method of claim 1, wherein the cause of Parkinsonism is progressive supranuclear palsy, multiple system atrophy, diffuse Lewy Body disease, drug-induced Parkinsonism, Creutzfeldt-Jakob disease or chronic brain trauma.

3. The method of claim 1, wherein Parkinson's disease is based on one or more genetic causes selected from GBA, LRRK2, SNCA, VPS35, Parkin, PINK1 and/or DJ1.

4. The method of claim 1, wherein the alpha-methyl-p-tyrosine is administered initially at a dose ranging from 1 mg daily up to 250 mg daily and then administered to a target maintenance dose at a range from 100 mg daily to 1000 grams daily.

5. The method of claim 1, wherein the composition is administered intra-nasally, and wherein the alpha-methyl-p-tyrosine is administered initially at a dose ranging from 0.01 mg daily up to 25 mg daily and then administered to a target maintenance dose ranging from 1 mg daily to 100 grams daily.

6. The method of claim 1, wherein the composition is administered in conjunction with levodopa, levodopa analog or dopaminergic containing medicines selected from dopamine receptor agonists, MAO-B inhibitors and/or COMT inhibitors.

7. The method of claim 6, wherein the doses of levodopa, levodopa analog or dopaminergic containing medication, selected from dopamine receptor agonists, MAO-B inhibitor and/or COMT inhibitor doses are adjusted during the initiation and ongoing administration of the composition containing alpha-methyl-p-tyrosine as clinically indicated.

8. The method of claim 1, wherein the composition is administered in conjunction with VMAT2 inhibitor(s).

9. The method of claim 1, wherein the alpha-methyl-p-tyrosine is deuterated in one or more positions where metabolism of alpha-methyl-p-tyrosine involves hydroxylation and/or carbonylation.

10. The method of claim 1, wherein the 3' and/or 5' positions of the benzene ring of the alpha-methyl-p-tyrosine are substituted with deuterium, a methyl group and/or any halide.

11. The method of claim 1, wherein the composition is administered with a urinary alkalinizing agent selected from the group consisting of sodium bicarbonate, calcium carbonate, sodium citrate, potassium citrate and calcium citrate.

12. The method of claim 11, wherein the urinary alkalinizing agent are administrated at a dose ranging from 5 to 300 mEq/day.

13. The method of claim 10, wherein the halide is fluoride, chloride, bromide, and/or iodide.

14. The method of claim 1, wherein the alpha-methyl-p-tyrosine is administered initially at a dose ranging from 1 μg to 25 g per day and then administered to a target maintenance dose at a range from 5 mg daily to 2000 mg daily.

15. The method of claim 1, wherein the alpha-methyl-p-tyrosine is administered initially at a dose ranging from 1 μg to 25 g per day and then administered to a target maintenance dose at a range from 500 mg daily to 2500 mg daily.

16. The method of claim 1, wherein the inhibitor of tyrosine hydroxylase is further one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr (TBU)-allyl ester HCl, methyl (2R)-2-amino-3-(3-chloro-4, 5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl)methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy]benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L tyrosine ethyl ester hydrochloride, DL-m-tyrosine, DL-o-tyrosine, Boc-Tyr (3,5-I2)-oSu, Fmoc-tyr $(3\text{-}NO_2)$—OH, α-methyl-L-tyrosine, α-methyl-D-tyrosine and/or α-methyl-DLtyrosine, aquayamycin, bulbocapnine, oudenone, 3-iodotyrosine, L-tryptophan, L-phenylalanine, DLp-fluoro-phenylalanine, and/or 3,4-dihydroxyphenylpropyl-acetamide (H-22/54), or pharmaceutical salts, esters, tartrates, gluconates, carbonates, anhydrous or free base forms thereof.

17. The method of claim 1 wherein the alpha-methyl-p-tyrosine is administered initially at a daily dose of about 50 mg and then administered to a target maintenance dose of up to about 1500 mg.

18. The method of claim 1, wherein the alpha-methyl-p-tyrosine is administered at a nominal dose of about 25 mg twice per day and then then administered in increased doses.

19. The method of claim 1, where the alpha-methyl-p-tyrosine is administered at 25 mg twice per day in week one, 50 mg twice per day in week two, 100 mg twice per day in week three, 100 mg three times per day in week four, 150 mg three times per day in week five, 200 mg three times per day in week six, 250 mg three times per day in week seven, 300 mg three times per day in week eight, 400 mg three times per day in week nine and 500 mg three times per day in week ten.

20. A method of treating movement disorders caused by Parkinson's disease and/or Parkinsonism by antagonizing tyrosine hydroxylase comprising administering to a human patient in need thereof, a composition comprising one or more of the competitive inhibitors of tyrosine hydroxylase including alpha-methyl-p-tyrosine, wherein the alpha-methyl-p-tyrosine is administered at a nominal dose or doses and then administered in therapeutic doses that are gradually increased over days or weeks.

21. A method of treating Parkinson's disease and/or Parkinsonism by antagonizing tyrosine hydroxylase comprising administering to a human patient in need thereof, a composition comprising alpha-methyl-p-tyrosine, wherein the alpha-methyl-p-tyrosine is administered at a nominal dose or doses and then administered in doses that are gradually increased over days or weeks to a dose or doses that act on the central nervous system.

22. A method of treating the movement disorder(s) associated with Parkinson's disease and/or Parkinsonism by antagonizing tyrosine hydroxylase comprising administering to a human patient in need thereof, a composition comprising alpha-methyl-p-tyrosine, wherein the alpha-methyl-p-tyrosine is administered at a nominal dose or doses and then administered in doses that are gradually increased over days or weeks to a dose or doses that act on the central nervous system.

23. The method of claim 1, wherein the alpha-methyl-p-tyrosine is L-alpha-methyl-p-tyrosine.

24. The method of claim 1, wherein the alpha-methyl-p-tyrosine is the racemic mixture of alpha-methyl-p-tyrosine.

25. The method of claim 16, wherein each of the compounds other than alpha-methyl-p-tyrosine is administrated at a dose ranging from 1 g to 25 g per day.

26. The method of claim 16, wherein each or any of the tyrosine hydroxylase inhibitors undergo substitution of hydrogen and/or hydroxy groups with deuterium, a methyl group and/or any halide.

27. The method of claim 26, wherein the halide is fluoride, chloride, bromide, and/or iodide.

* * * * *